United States Patent [19]

Kea et al.

[11] Patent Number: 4,683,299

[45] Date of Patent: Jul. 28, 1987

[54] SUGAR ESTERS AND AN IMPROVED ANHYDROUS METHOD OF MANUFACTURE

[75] Inventors: Sandra Kea; Charles E. Walker, both of Lincoln, Nebr.; Eric Kline, Austin, Tex.

[73] Assignee: Nebraska Department of Economic Development, Lincoln, Nebr.

[21] Appl. No.: 639,784

[22] Filed: Aug. 10, 1984

[51] Int. Cl.$^4$ .............................................. C07H 1/00
[52] U.S. Cl. ...................................... 536/119; 536/115
[58] Field of Search ........................ 536/119, 18.2, 115

[56] References Cited

U.S. PATENT DOCUMENTS

| | | | |
|---|---|---|---|
| 1,959,590 | 5/1934 | Lorand | 536/119 |
| 2,759,922 | 8/1956 | Gibbons | 536/18.2 |
| 2,948,717 | 8/1960 | Babayan et al. | 536/119 |
| 3,249,600 | 5/1966 | Nobile et al. | 536/119 |
| 3,714,144 | 1/1973 | Feuge et al. | 536/119 |
| 3,748,324 | 7/1973 | Mizutani et al. | 536/119 |
| 3,956,278 | 5/1976 | Prey | 536/119 |

OTHER PUBLICATIONS

A Solventless Process and the Products Thereof, James, J.; Hurford, J.; Parker, K. J., American Chemical Society, 1976, 172, Carb 73.
Quantitative Estimation of Sucrose Esters of Palmitic Acid, Weis, T. J.; Brown, M.; Zeringue, H. J.; Feuge, R. O., J. Am. Oil Chem. Soc. 48 (4): 145–148, 1971.
Purification of Sugar Esters by Ultrafiltration, Zeringue, H. J. Jr.; Feuge, R. O., J. Am. Oil Chem. Soc. 53 (12): 719–721, Dec. 1976.
Purification of Sucrose Esters by Selective Adsorption, Zeringue, H. J.; Feuge, R. O., J. Am. Oil Chem. Soc. 53(9): 567–571, Sep. 1976.
Influence of Solvent on Degree of Acylation in the Formation of Sucrose Esters, Weis, T. J.; Brown, M.; Zeringue, H. J.; Feuge, R. O., J. Am. Oil Chem. Soc. 49 (9): 524–526, Sep. 1972.
Preparation of Sucrose Esters by Interesterification, Feuge, R. O.; Zeringue, H. J.; Weis, T. J.; Brown, M.; J. Am. Oil Chem. Soc. 47 (20): 56–60, Feb. 1970.
A Solvent-Free Synthesis of Sucrose Polyesters, Rizzi, G. P.; Taylor, H. M.; J. Am. Oil Chem. Soc. 55 (4): 398–401, 1978.
Sucrose Ester Surfactants–A Solventless Process and the Products Thereof—Parker, J. J.; James, K.; Hurford, J.; Journal: ACS Symp. Ser.—Publ.: 1977, Series: 41 Issue: Sucrochem., Symp., 1976—pp. 97–114.
Vogel's Practical Organic Chemistry 4th Edition, Longman, 1978, pp. 456–457.

*Primary Examiner*—Johnnie R. Brown
*Attorney, Agent, or Firm*—Lucas & Just

[57] ABSTRACT

The invention relates to an improved process for the synthesis of sugar esters carried out in a substantially anhydrous system and in the presence of an organic acid chloride. Any of the known available sugars may be used and in particular hydrolyzate sugars derived from starch are effectively employed in accordance with the present invention to produce sugar esters having superior emulsifying characteristics for use as an ingredient in food products for human consumption.

21 Claims, No Drawings

SUGAR ESTERS AND AN IMPROVED ANHYDROUS METHOD OF MANUFACTURE

The present invention relates to sugar esters which have superior emulsifying characteristics and are especially adapted for use as an ingredient in a variety of food products and pharmaceuticals. The invention also relates to a new and practical process for the manufacture of such sugar esters.

Sugar esters have been prepared heretofore by organic synthesis wherein sucrose is reacted with an ester of a long chain, 12 to 22, carbon atom fatty acid in aqueous solution as described in U.S. Pat. No. 3,644,333. It has also been suggested to react sucrose with a long chain fatty acid chloride in aqueous solution to form sucrose esters as described in U.S. Pat. No. 2,948,717.

The prior art aqueous system has the drawback of hydrolysis that takes place when the selected reagent is the salt of a fatty acid which reverts back to its acid form in water and thereby becomes ineffective for producing sucrose esters. Aqueous systems may also require special care in preparing a transparent microemulsion for the organic synthesis in order to obtain a sufficiently high yield to make the process attractive for practical commercial use. Moreover as described in U.S. Pat. No. 3,748,324, purification of the sugar ester product is difficult to achieve and frequently involves the use of toxic solvents at some stage in the process which necessitates the difficulty and expense of removing toxic materials if the sucrose ester is to be used as an ingredient in food products.

These drawbacks have now been overcome and in accordance with the present invention, sugar esters are synthesized in a substantially anhydrous organic liquid solvent system in the presence of an organic acid chloride to produce non-toxic edible sugar esters particularly adapted for use in human food products. For best results, a catalyst is employed to expedite synthesis and to provide a high yield of sugar esters.

One preferred method of practicing the present invention involves the step of adding a selected sugar to a liquid solvent such as acetic acid. This step is best carried out by employing vigorous agitation and gentle heat such as about 90° C. and above to aid in dissolving as much sugar as possible in the solvent without burning or charring the selected sugar.

It is important that virtually no water be present in the system and for best results an anhydrous liquid system is employed. To this end, glacial acetic acid is preferred over acetic acid and the selected sugar should have a low moisture content preferably below about 5% by weight moisture (dry basis). In order to provide an anhydrous system, a dry gas purge is preferably employed to strip moisture from the liquid reaction system while the sugar is being added and thereafter during reaction. An inert gas purge such as a dry nitrogen gas purge is used to advantage for stripping water from the system. In addition, some of the glacial acetic acid may be distilled off under reduced pressure of about 430–600mm Hg. vacuum to insure an anhydrous perfectly dry reaction system. The nitrogen gas purge is interrupted while up to about 20% by weight of the solvent is distilled off. While an inert gas purge is a most convenient way to obtain an anhydrous liquid reaction system, it will be understood that any conventional method may be employed to establish a substantially anhydrous reaction system.

The next step in the process is to add a selected organic acid chloride such as palmitoyl chloride to the system for reaction with the sugar. The organic acid chloride is slowly added to the sugar solvent system with continuous agitation and the nitrogen purge is also preferably continued to maintain an anhydrous reaction system. Reaction is best carried out with continuous agitation and at any selected temperature depending on the equipment at hand. Care should be taken to avoid burning and charring of the selected sugar since such degradation will impair the quality of the sugar ester and materially reduce yields and make it extremely difficult or virtually impossible to separate the desired sugar ester from the reaction mass for subsequent refinement for use as a food product ingredient. In general, best results are achieved by carrying out the reaction at a temperature of at least about ambient room temperature and up to about 250° C. or more.

It has been found to be of advantage to initiate reaction by adding the selected organic acid chloride slowly to the sugar-solvent mixture at relatively low temperature of about 90° to about 116° C. Thereafter, the reaction mass may be cooled to about 80° C. to complete the reaction in about 35 minutes or less. Reaction may also be carried out at lower temperatures of from about 30° to 55° C. but the time for complete reaction will be increased and may range up to about 24 to 60 hours. The addition of the organic acid chloride to the sugar-solvent mixture at a temperature of at least about 85° to 90° C. and above is of advantage to prevent sugar from precipitating out from the solvent when reaction is carried out at lower temperatures of about 30° to 55° C. Those of skill in the art will have no difficulty in determining the proper time and temperature relationship for the equipment at hand to avoid degeneration of the reactants which could result in a poor yield of sugar esters and a low quality product.

Best results are achieved by adding a catalyst such as potassium carbonate to the sugar mixture before adding the organic acid chloride. The catalyst is effective for ease of reaction and high sugar ester yields. The sugar esters may be conveniently recovered as the residue that remains after distilling off the solvent. The sugar esters may be used as recovered or further refined in conventional manner.

Another great advantage of the present invention involves the use of any of the known available edible sugars as compared to prior art processes which are only effective with sucrose. Starch hydrolyzate sugars derived from corn, wheat, rice, milo, potato, etc. starches both the waxy and non-waxy varieties converted with either acid or enzymes or both as well as sucrose, fructose and other sugars or sugar substances such as the sugar alcohols e.g. manitol may be used to produce sugar esters in accordance with the present invention. As is known, starch hydrolyzate sugars may be virtually pure such as the monosaccharide glucose (dextrose), the disaccharide, maltose, triose and on up to the very long molecular chain dextrins which are not at all sweet. Alternatively, a mixture of starch hydrolyzate sugars may be employed such as those sold as corn syrup solids rated by DE (dextrose equivalent value) which indicates the level of reducing sugar content measured on a scale of 0 to 100% dextrose. These corn syrup solids starch hydrolyzate sugars are a mixture of sugars starting with the monosaccharide, dextrose, the disaccharide, maltose and on up to the very long chain dextrins and the sweetness of the sugar increases with increasing DE. Corn syrup solids of about 1.0 to 20 DE have virtually no discernible sweetness and are used as food product ingredients for their functional characteristics such as bulking, bodying, or coating agents, carriers, spray drying adjuncts, and for their encapsulating characteristics for flavors. The higher DE corn syrup solids of above about 25 DE do impart some sweetness and these are also used for their functional characteristics in food products. Corn syrup solids are conventionally employed in a wide variety of food products such as baked goods, beverages, soups, spices, seasonings, artificial sweeteners, coffee whiteners, dairy products, ice cream, deserts, toppings, meat products, etc. This flexibility in selection of one or more of the available sugars coupled with the functionality of superior emulsifying characteristics provides sugar esters in accordance with the present invention which are of particular advantage for use as food product ingredients.

The term sugar used in the description and claims means any of the known corn syrup solid hydrolyzate sugars such as dextrose, maltose, triose, etc. and mixtures thereof of any selected DE as well as fructose, sucrose, lactose, cellobioise and sugar alcohols or mixtures thereof which occur in nature or are manufactured.

The organic acid chlorides used in the sugar ester synthesis in accordance with the present invention include substantially anhydrous organic acid chlorides or anhydrides thereof having at least 2 carbon atoms such as the chloride of acetic acid up to the higher fatty acid chlorides containing 22 and more carbon atoms and preferably up to 16.0 carbon atoms such as palmitoyl chloride which is a preferred organic acid chloride used in synthesizing the sugar esters of the present invention. The selected organic acid chloride may be used alone or in combination with one or more other organic acid chlorides. These organic acid chlorides are effective for producing non-toxic and edible sugar esters which are used to great advantage in edible food products for human consumption.

The term organic acid chloride used in the description and claims includes one or more organic acid chlorides and anhydrides thereof having at least 2 carbon atoms and up to 22 carbon atoms or more.

It has also been found that organic fatty acids containing from 2 carbon atoms up to 22 and more carbon atoms, the anhydrides, esters and glyceride esters thereof such as occur in vegetable and animal fats and oils in the presence of the organic acid chloride will enter into the synthesis reaction and become attached to the sugar in various substitutions. More specifically, it has been found that acetic acid could not be used alone for synthesis with the sugars but was readily used in the synthesis to attach acetates in various substitutions when an organic acid chloride such as palmitoyl chloride was used in combination with the acetic acid. While we do not now understand the mechanism of reaction, it is believed that the formation of sugar palmitates in some way initiates and makes the synthesis of sugar acetates possible. The combination of a mixture of palmitates and acetates attached to the sugar molecules has been found to provide a mixed sugar esters having unexpectedly superior emulsifying characteristics as ingredients in food products. The selected organic fatty acid, anhydrides, esters and glyceride esters thereof may be used alone or in combination to form sugar esters in the presence of the selected organic acid chloride in accordance with the present invention. Animal or vegetable fats or oils may be used as a source of glyceride esters for sugar ester synthesis in accordance with the present invention. In general, the amount of sugar ester produced is directly related to the amount of palmitoyl chloride or other organic acid chloride present in the anhydrous reaction mixture.

The amount of sugar selected for reaction with the selected organic acid chloride may be varied but in general from about 0.1 moles to about 10.0 moles of organic acid chloride for each monosaccharide moiety may be used. Best results are achieved by using from about 1.0 to 1.5 moles of sugar for each 1.0 mole of organic acid chloride. Theoretically, 1.0 mole of the selected organic acid chloride reacts with 1.0 mole of the selected sugar to form a mono-ester. It has been found that an excess of sugar over the 1.0 to 1.0 mole ratio will provide a much higher yield of product since the theoretical stoichiometric substitution is not necessarily obtained. In general, a mono-ester is formed at the 1.5 to 1.0 mole ratio of sugar to organic acid chloride. Di-esters, tri-esters, etc. may be produced by increasing the mole ratio of the organic acid chloride to sugar. Thus for the di-ester, two moles of organic acid chloride are used for each one and one-half moles of sugar whether it be a monosaccharide or disaccharide, etc. or mixtures thereof. Increasing the amount of organic acid chloride will tend to produce sugar di-esters but the resulting product will be a mixture of the di-ester and mono-ester sugars. One or more organic fatty acids having at least 2 carbon atoms and up to 22 and more carbon atoms, the anhydrides, esters and glyceride esters thereof as well as vegetable and animal fats and oils may be added to the reaction mixture. These fatty acid materials either alone or in combination will react in the presence of the organic acid chloride and be added onto the selected sugar in various position substitutions to form mixed sugar esters. The amount of these fatty acid materials may be varied depending on the properties desired in the sugar ester product. The fatty acid materials may be substituted for part of the organic acid chloride but in any event there will be at least about 0.1 mole of organic acid chloride for each mole of sugar in the reaction mixture to provide transesterification to sugar esters. The total amount of organic acid chloride in combination can be a maximum that theoretically will react to synthesize sugar esters. In general the total amount of organic acid chloride and fatty acid materials will not be more than about 10.0 moles for each mole of monosaccharide moiety. Other esters, alcohols (mono or polyhydric) and fatty acid materials may also be added to the reaction mixture as long as these do not exclude synthesis of sugar esters by the organic acid chloride. In accordance with the present invention, all ingredients are substantially anhydrous to avoid the need for removing objectionable moisture prior to reaction with the organic acid chloride and preferably all of the resulting sugar esters are non-toxic and suitable for human consumption.

The term fatty acid material used in the specification and claims means one or more organic fatty acids having at least 2 carbon atoms, the anhydrides, esters and glyceride esters thereof and non-toxic edible vegetable and animal fats and oils containing glyceride esters.

Any substantially anhydrous liquid solvent that will dissolve, suspend or hold sugar in a colloidal dispersion may be used in the reaction mixture to expedite vigorous agitation for contact of the reactants for the desired transesterification to produce sugar esters.

Some solvents that may be used include acetic acid, glacial acetic acid, propionic acid and buteryic acid or any other non-toxic organic acid that is a liquid at the synthesis reaction temperature and which will dissolve, suspend or colloidally disperse the selected sugar for reaction with the organic acid chloride. The organic acid chlorides or the above-specified fatty acid material or mono or polyhydric alcohols such as glycerol may also be used as the solvent for the synthesis reaction.

Fatty acid material and the fatty acids are the preferred solvents which as in the case of acetic acid quite unexpectedly attach to the sugar molecule in the presence of the selected organic acid chloride to provide a mixed ester of superior emulsifying characteristics for use as an ingredient in food products. One or more organic acid chlorides may be used as the only solvent for the synthesis reaction. A combination of two or more organic acid chlorides will produce mixed sugar esters such as a combination of 50% palimotyl chloride and 50% stearoyl chloride. When a single organic acid chloride such as lauroyl chloride is used alone as the solvent and for synthesis, the sugar ester will only have attached laurate groups. The amount of solvent employed will vary depending on the manufacturing equipment at hand. In the case of acetic acid it has been found convenient to use from about 1.0 ml. to about 100.0 ml. for each 0.001 moles of organic acid chloride and preferably about 5.0 ml. for each 0.001 moles of organic acid chloride.

The term solvent used in the description and claims means any substantially anhydrous material that is a liquid at the synthesis reaction temperature and pressure and will dissolve, suspend or hold sugar in a colloidal dispersion for synthesis reaction with the selected organic acid chloride.

For best results in ease of reaction and high yields, a catalyst is added to the reaction mixture. The catalyst may be any of the mono or divalent basic salts of a weak acid. Suitable catalysts include potassium palmitate, potassium carbonate, potassium chromate and calcium proprionate. The amount of catalyst will vary and in general from about 0.01 mole to about 1.0 mole of catalyst may be employed for each 1.0 mole of organic acid chloride. Preferably about 0.079 moles of catalyst is employed for each 1.0 mole of organic acid chloride with excellent results. The catalyst is preferably added to the reaction mixture prior to adding the organic acid chloride. Heat may also serve as a catalyst for stimulating reaction.

Use of an excess of sugar over the stoichiometric amount required for reaction with the selected organic acid chloride will in general increase the yield of sugar ester. Thus, for example, an excess of corn syrup solids sugar over the stoichiometric amount for synthesis with palmitoyl chloride in glacial acetic acid, has resulted in yields of about 97.5% and 99.47% of the theoretical stoichiometric amount of mono-ester. It has been determined that during reaction palmitates are formed in various substitutions and in addition the solvent also reacted to attach acetates in various substitutions on the saccharides. This probably accounts for the unexpectedly high yield of sugar esters that have been obtained in accordance with the present invention.

Sugar esters made in accordance with the present invention tested for their emulsifying properties in cake batters showed superior characteristics in imparting improved batter characteristics and superior textures and volume to the finished baked goods as compared to prior art sucrose sugar esters. The volumes of cakes using the sugar esters of the present invention were increased by up to about 25% by volume over that obtained with the prior art sucrose esters and the texture of the batter was creamy and smooth as compared to the somewhat curdled texture of the batters made with the prior art sucrose esters.

Further details and advantages of the present invention will be apparent from the following detailed examples illustrating a few preferred embodiments of producing sugar esters in accordance with the present invention.

EXAMPLE I 50 ml. of glacial acetic acid were heated to 90° C. in a conventional reaction vessel Dry nitrogen gas was purged through the reaction vessel and then 0.015 mole of maltose were added with vigorous stirring while the temperature was maintained at 90° C. and the nitrogen gas purge was continued to maintain a dry atmosphere. After all the maltose had been added and suspended in the acetic acid the nitrogen gas purge was interrupted. The temperature was dropped to 70° C. and the vessel was subjected to reduced pressure of about 600 mm Hg. vacuum in order to distill off about 10 ml. of the acetic acid to make sure that any moisture present in the reaction vessel was removed and that the mixture was in an anhydrous condition. Thereupon the vacuum was removed and 0.00079 mole of potassium carbonate was added and then 0.01 mole of palmitoyl chloride was added dropwise with continuous vigorous agitation and nitrogen gas purge. Heating was discontinued after 1.0 ml. of palmitoyl chloride was added and the mixture was cooled to 70° C. while the remainder of the palmitoyl chloride was slowly added. The mixture was allowed to cool slowly to 40°–55° C. and it was held at this temperature for 15 hours with continued agitation and nitrogen gas purge. Reaction to synthesize sugar esters was indicated by the mixture becoming light yellow when the reaction was initiated and darker as reaction continued. At the end of 15 hours the acetic acid was distilled off leaving a residue of sugar esters. The yield of mixed maltose sugar ester was 97.25% by weight of the theoretical stoichiometric yield of the monoester. It was determined that acetate groups as well as palmitate groups had become attached to the sugar which was of advantage for the high yield obtained in accordance with the present invention.

EXAMPLE II 50 ml. of glacial acetic acid were heated in a conventional reaction vessel to 110° C. A dry nitrogen gas purge was started and 0.015 mole of sucrose was added with vigorous agitation while the nitrogen gas purge was continued. After the sugar was suspended in the glacial acetic acid, 10.0 ml. of acetic acid were distilled off under reduced pressure (300 mm Hg. vacuum). The nitrogen gas purge was discontinued during distillation. The reaction mixture was cooled down to about 86° C. whereupon 0.01 mole of palmitoyl chloride was added dropwise to the reaction mixture while under nitrogen gas purge and vigorous agitation. The reaction mixture was allowed to cool to 40° to 50° C. and was held at this temperature for about 13 hours with continuous nitrogen gas purge and vigorous agitation. The remaining acetic acid was then distilled off under reduced pressure leaving a golden solid residue of mixed palmitate and acetate sugar esters. The yield of mixed sugar esters was 80.7% by weight of the theoretical stoichiometric yield of the monoester.

EXAMPLE III

The procedure of Example I was repeated using 200 ml of glacial acetic acid, 20.636 grams maltose, 11.026 grams of palmitoyl chloride and 0.45 gram of potassium carbonate. Reaction was allowed to continue for 50 hours whereupon the mixed sugar esters were recovered from the reaction mass. The yield of sugar ester recovered was 99.47% of the theoretical yield.

EXAMPLE IV

The procedure of Example I was repeated using 50 ml of glacial acetic acid, 2.703 grams of glucose, 0.144 gram of potassium carbonate and 2.752 grams of palmitoyl chloride. The glacial acetic acid was heated to 94° C. whereupon the sugar was slowly added and a nitrogen gas purge was initiated and continued throughout the reaction. 10 ml acetic acid were distilled off under vacuum of 575mm Hg. The vacuum was discontinued and temperature of the mixture was raised to 110° C. to dissolve the glucose in the acetic acid. Temperature was reduced to 87° C. and the potassium carbonate catalyst was added and then the palmitoyl chloride was slowly added while the temperature of the reaction mixture dropped to 59° C. Reaction at 59° C. under the nitrogen gas purge was continued for 18 hours. The yield of mixed sugar esters was 90.9% of the theoretical yield.

EXAMPLE V

In this example 0.081 mole of palmitoyl chloride were heated to 60° C. and held under nitrogen gas purge while 0.015 mole of maltose along with 0.00079 mole of potassium carbonate were added with vigorous agitation. Reaction was allowed to continue for 15 hours with agitation and nitrogen gas purge at reduced temperature of 40° to 45° C. A precipitate of maltose palmitate sugar ester was recovered after distilling off the remaining palmitoyl chloride. The recovery was 85% by weight of the theoretical stoichiometric yield of monoester.

EXAMPLE VI

The procedure of Example V is repeated using the same amounts of ingredients except that lauroyl chloride is used in place of the palmitoyl chloride and glucose is used in place of the maltose sugar. The glucose sugar ester is recovered after distilling off the remaining lauroyl chloride.

EXAMPLE VII 50 ml. of glacial acetic acid were heated to 116° C. at which time 5.15 grams (or approximately 0.015 mole) of 42 DE corn syrup solids were dissolved therein. A total of 0.01 mole of palmitoyl chloride was used for reaction. About 1.25 ml of the palmitoyl chloride were initially added and heating was discontinued. When temperature dropped to 100° C., 0.00079 mole of potassium carbonate was charged. At 95° C. the remaining 0.006 mole of palmitoyl chloride was slowly dropped into the vessel while the temperature dropped to 40°-50° C. over a period of 1½ hours. The temperature was maintained at 40°-50° C. and reaction ran for 15 hours with a yield of 97% of mixed sugar esters.

EXAMPLE VII

The procedure of Example I was repeated using 50 ml glacial acetic acid, 0.015 mole maltose, 0.00079 mole potassium carbonate, 0.005 mole palmitoyl chloride and 0.005 mole of acetyl chloride.

The palmitoyl chloride was added to the sugar solution at 94° C. and the temperature was allowed to increase to 106° C. whereupon the acetyl chloride was slowly added and the temperature was allowed to drop to 80° C. and reaction was terminated. The mixed sugar ester was recovered after 35 minutes total reaction time with a yield of 138% of mixed sugar esters.

EXAMPLE IX

The procedure of Example I was repeated using 50 ml glacial acetic acid, 5.161 grams of maltose, 0.115 gram of potassium carbonate, 1.374 grams of palmitoyl chloride and 1.519 grams of stearoyl chloride.

The maltose was dissolved in the acetic acid heated to 95° C. and 10 ml of acetic acid were distilled off at 92° C. and under a vacuum of 600 mm Hg. The potassium carbonate was added followed by the slow addition of the palmitoyl chloride and then the stearoyl chloride was added to the reaction mixture. The mixture was held at about 100° C. while the organic acid chlorides were added and a constant nitrogen gas purge was started when the sugar was added and maintained throughout the reaction except during the acetic acid distillation. Total reaction time between the maltose and organic acid chlorides was 35 minutes. The yield of mixed sugar esters was 114% of the theoretical yield.

EXAMPLE X

In this example 50 ml of glacial acetic acid were heated to 95° C. and 5.15 grams of maltose were dissolved in the acetic acid under a nitrogen gas purge. The nitrogen gas purge was interrupted while 10 ml of acetic acid were distilled off at 85° C. under vacuum of 575 mm Hg. Thereafter the nitrogen gas purge was resumed and 0.135 gram of potassium carbonate was slowly added followed by the very slow addition of 0.785 gram of acetyl chloride. Reaction at about 70° C. under the nitrogen gas purge was continued for 33 hours. The acetic acid was distilled off to recover the acetate sugar esters.

EXAMPLE XI

The procedure of Example I was used for the synthesis reaction of maltose with palmitoyl chloride in the presence of glacial acetic acid and calcium proprionate catalyst. 50 ml glacial acetic acid were heated to 94° C. and 5.161 grams of maltose were dissolved in the acetic acid under a nitrogen gas purge. The gas purge was interrupted while 10 ml of acetic acid were distilled off at 90° C. under a vacuum of 640 mm Hg. After distillation the nitrogen gas purge was resumed and 0.156 gram of calcium proprionate catalyst was added followed by the slow addition of 2.832 grams of palmitoyl chloride. Reaction at 102° C. under the nitrogen gas purge was continued for 18 hours. The acetic acid was distilled off under vacuum. The yield of mixed sugar esters was 115% of the theoretical yield.

EXAMPLE XII

The procedure of Example I was repeated using 50 ml glacial acetic acid, 5.152 grams of maltose, 0.156 gram of potassium chromate catalyst and 2.762 grams of palmitoyl chloride.

The maltose was added to the glacial acetic acid heated to a temperature of 90° C. and under a nitrogen gas purge. The gas purge was interrupted and 10 ml of acetic acid were distilled off under a vacuum of 675 mm Hg. After distillation the nitrogen gas purge was resumed and maintained throughout the reaction. The temperature of the mixture was maintained at 86°–90° C. while the potassium chromate catalyst was added followed by the slow addition of the palmitoyl chloride. Reaction was allowed to continue for 18 hours at 86°–90° C. The sugar esters were recovered by distilling off the acetic acid.

EXAMPLE XIII

White cakes were prepared and baked, using the standard procedure of the American Association of Cereal Chemists (AACC), to compare the emulsifying characteristics of the sugar esters of the present invention with prior art sucrose sugar esters.

The following AACC standard procedure was used in baking the cakes used in this Example as follows:
Baking
Use 6 inch cake pans.
Heat oven to 375° F., bake cakes for 19 minutes, cool 30 minutes, remove from pan and cool 30 minutes, measure.
Batter Mix

| | |
|---|---|
| Cake flour at 14% moisture | 111.28 g |
| Extra-fine granulated sugar | 155.79 g |
| Shortening | 55.64 g |
| Nonfat dry milk | 13.35 g |
| Salt | 3.34 g |
| Baking powder | 5.84 g |
| Egg white | 10.02 g |
| Distilled water | 144.66 g |

Grease and line baking pans with waxed paper. Sift dry ingredients twice.
1. Cream shortening for 1 minute at speed 6 of the Hobart K5a mixer.
2. Scrape down bowl. Add dry ingredients and all but 60 mls. of H$_2$O.
Mix 30 seconds on low speed.
3. Scrape bowl and beaters. Mix 4 minutes at speed 6.
4. Scrape. Add 30 mls. of water. Mix 30 seconds at low speed.
5. Scrape. Mix 2 minutes at speed 6.
6. Scrape. Add 30 mls. of water. Mix 30 seconds at low speed.
7. Scrape. Mix 2 minutes at speed 6.
8. Tare pan and add about 235 g of batter.
To adjust flour to 14% mwb:

$$\text{amount of flour used} = X$$

$$(111.28 \text{ g})(0.86) = \frac{(100 - \% \text{ moisture}) X}{100}$$

Measure diameter of cake (measured 1 cm from bottom).
Measure height of cake using the template.

$$\text{Volume (cm}^3\text{)} = \frac{D^2 \cdot \pi \cdot (B + C + D)}{12}$$

1.1 grams of the maltose sugar ester prepared in accordance with Example I were added to the batter of cake A and 1.1 grams of sucrose sugar ester supplied by Dai-Ichi Kogyo Seiyaku Co. and described in U.S. Pat. No. 3,748,324 were added to the batter of cake B. In each case the amount of added sugar ester was subtracted from the dry weights of the cake flour. The sugar esters used in the cakes were each of comparable low degree of substitution. Cake A and cake B were of equal batter weight and baked and measured for volume as specified above.

The volume of cake A was measured to be 680 cm$^3$ while the volume of cake B was only 540 cm$^3$. The texture of the batter of cake A was observed to be creamy and smooth while the texture of the batter of cake B was curdled and rough.

EXAMPLE XIV

Example XIII was repeated except that the sugar esters produced in accordance with Example III hereinabove were used in cake C instead of the sugar esters of Example I. Cake D was identical to cake B and the sugar esters in both cakes C and D were of a comparable low degree of substitution.

The volume of cake C was 570 cm$^3$ while the volume of cake D was 490 cm$^3$. The texture of the batter of cake C was relatively smooth and only slightly curdled while the texture of the batter of cake D was observed to be definitely curdled.

These Examples show the superior emulsifying properties of the sugar esters of the present invention over the sugar esters of the prior art.

It will be understood that it is intended to cover all changes and modifications of the preferred embodiment of the invention herein chosen for the purpose of illustration which do not constitute a departure from the spirit and scope of the invention.

What is claimed is:

1. A method for synthesizing sugar esters which comprises the steps of:
    (a) dissolving an edible sugar in a subsantially anhydrous organic acid solvent;
    (b) adding to said solvent and said dissolved edible sugar an organic acid chloride having at least two carbon atoms to form a substantially anhydrous liquid mixture containing at least about 0.1 mole of organic acid chloride for each mole of monosaccharide moiety of sugar;
    (c) mixing said sugar and organic acid chloride to cause an esterification reaction;
    (d) maintaining a substantially anhydrous condition throughout the reaction; and
    (e) recovering the sugar ester thereby produced.

2. The method of claim 1 in which the organic acid chloride is the chloride of acetic acid.

3. The method of claim 1 in which the organic acid chloride is palmitoyl chloride.

4. The method of claim 1 in which the solvent is acetic acid or glacial acetic acid.

5. The method of claim 1 which includes the step of adding fatty acid material to the said mixture before the esterification reaction.

6. The method of claim 1 in which the sugar is one or more hydrolyzate sugars derived from starch.

7. The method of claim 1 which includes the step of adding a catalyst to the mixture to stimulate the esterification reaction.

8. A method for synthesizing sugar esters in a reaction vessel which comprises the steps of:
(a) adding an edible sugar to a substantially anhydrous organic acid solvent in said reaction vessel;
(b) agitating the resulting liquid mixture to disperse the sugar therein;
(c) purging the reaction vessel with a dry inert gas to remove moisture therefrom;
(d) adding to said mixture an organic acid chloride having from about 2 to about 22 carbon atoms in an amount of at least about 0.1 mole of organic acid chloride for each mole of sugar for reaction with said sugar;
(e) adding a catalyst to the mixture to stimulate reaction;
(f) agitating the mixture to cause an esterification reaction between the sugar and organic acid chloride;
(g) continuing said purging of the reaction vessel with said dry inert gas to remove moisture therefrom throughout the reaction; and
(h) recovering the sugar ester of the esterification raction from said mixture.

9. The method of claim 8 wherein the solvent is acetic acid or glacial acetic acid and the sugar is one or more hydrolyzate sugars derived from starch.

10. The method of claim 9 which includes the step of forming a sugar mixed ester by adding an organic acid chloride having at least 3 carbon atoms for the esterification reaction with the sugar.

11. The method of claim 9 which includes the step of forming a sugar mixed ester by adding palmitoyl chloride as the selected organic acid chloride.

12. The method of claim 9 wherein the solvent is heated to a temperature of at least about 90° C. to dissolve the one or more starch hydrolyzate sugars in the solvent.

13. The method of claim 12 in which the sugar is maltose or glucose.

14. The method of claim 8 in which the catalyst is potassium palmitate or potassium carbonate.

15. The method of claim 8 which includes the step of adding fatty acid material to the mixture before the esterification reaction.

16. The method of claim 8 in which the organic acid chloride is the solvent used in forming said mixture.

17. The method of claim 16 in which the organic acid chloride is palmitoyl chloride or acetyl chloride.

18. The method of claim 12 in which the esterification reaction is carried out at a temperature between about 30° to 55° C.

19. A method for producing a starch hydrolyzate sugar mixed ester (in a subtantially anhydrous environment) which comprises the steps of:
(a) dissolving one or more starch hydrolyzate sugars in an acetic acid solvent;
(b) subjecting the resulting sugar and acetic acid mixture to agitation;
(c) providing a dry inert gas purge;
(d) adding palmitoyl chloride to the resulting sugar and acetic acid mixture in an amount of from at least about 0.1 mole of palmitoyl chloride for each 1.0 mole of sugar;
(e) adding a catalyst to stimulate an esterification reaction;
(f) agitating the sugar, acetic acid and palmitoyl chloride mixture while continuing the dry inert gas purge to cause an esterification reaction between the hydrolyzate sugar, palmitoyl chloride, and acetic acid; and
(g) recovering the hydrolyzate sugar mixed palmitate and acetate ester.

20. A method for synthesizing sugar esters which comprises the steps of:
(a) forming a substantially anhydrous reaction mixture by adding an edible sugar to a substantially anhydrous organic acid liquid solvent;
(b) adding to the resulting mixture an edible organic acid chloride having from about 2 to about 22 carbon atoms for reaction with said sugar;
(c) subjecting said mixture of sugar, solvent and acid chloride to agitation to cause esterification reaction between said sugar and organic acid chloride;
(d) maintaining a substantially anhydrous environment throughout the reaction; and
(e) recovering the sugar ester of said reaction from the mixture.

21. A method for synthesizing sugar esters by interesterification of sugar with an organic acid chloride which comprises the steps of:
(a) adding sugar to a substantially anhydrous liquid organic acid solvent in which a substantially anhydrous liquid organic acid chloride has already been added, said organic acid chloride having at least two carbon atoms;
(b) mixing said sugar and organic acid chloride to cause interesterification;
(c) maintaining a substantially anhydrous condition throughout the reaction; and
(d) recovering the sugar ester so produced.

* * * * *